United States Patent [19]
Bridges

[11] Patent Number: 5,326,530
[45] Date of Patent: Jul. 5, 1994

[54] ENERGY-EFFICIENT ELECTROMAGNETIC ELIMINATION OF NOXIOUS BIOLOGICAL ORGANISMS

[75] Inventor: Jack E. Bridges, Park Ridge, Ill.

[73] Assignee: IIT Research Institute, Chicago, Ill.

[21] Appl. No.: 643,332

[22] Filed: Jan. 22, 1991

[51] Int. Cl.$^5$ ................................................ A61L 2/00
[52] U.S. Cl. ........................................ 422/22; 422/21
[58] Field of Search ..................................... 422/20–22

[56] References Cited

U.S. PATENT DOCUMENTS

| | | |
|---|---|---|
| 1,934,704 | 11/1933 | Golden . |
| 3,095,359 | 6/1963 | Heller . |
| 3,265,605 | 8/1966 | Doevenspeck . |
| 4,207,286 | 6/1980 | Gut Boucher ........................ 422/22 |
| 4,457,221 | 7/1984 | Geren . |
| 4,572,775 | 2/1986 | Paniagua . |
| 4,695,472 | 9/1987 | Dunn et al. . |
| 4,838,154 | 6/1989 | Dunn et al. . |

OTHER PUBLICATIONS

"Study of Reagentless Sterilization of Wastewaters" Journal of Applied Chemistry of the USSR, vol. 59, #11, pp. 2365–2368 Nov. 1986, Markitanova et al.

*Primary Examiner*—Lyle A. Alexander
*Attorney, Agent, or Firm*—Dorn, McEachran, Jambor & Keating

[57] ABSTRACT

An energy-efficient method for killing noxious biological organisms (bacteria, insects, etc.) in contaminated materials ranging from liquid, semi-liquid, and solid foods pharmaceuticals and hospital wastes comprises passing the contaminated material through an exposure chamber; screening, comminution, addition of fluid or foam, limited heating, or other pretreatment steps may be required. As it flows through the exposure chamber the contaminated material is subjected to a nonuniform, high-intensity electric field; in that chamber, excessive current flows, including arcing and current "streamers", are suppressed by limiting the current density. The amplitude of the applied current density and the electric field in the exposure chamber are controlled, in accordance with the conductivity and/or dielectric constant of the contaminated material, so that the electric field intensity is of the order of 3,000 volts/centimeter or more.

19 Claims, 8 Drawing Sheets

FIG. 16A — GRID VOLTAGE 461

FIG. 16B — PLATE VOLTAGE 462

FIG. 16C — POWER SUPPLY CURRENT 463

ENERGY-EFFICIENT ELECTROMAGNETIC ELIMINATION OF NOXIOUS BIOLOGICAL ORGANISMS

BACKGROUND OF THE INVENTION

The treatment of food, waste, drugs and medical products to inactivate noxious biological organisms is currently being done by thermal, chemical and ionizing radiation processes. For example, the use of chlorine to treat water creates chlorine-related chemicals which may be carcinogenic and which often causes eye irritations in swimming pools. The use of heat to sterilize or pasteurize food often changes the taste and flavor. Similarly, in the case of nuclear radiation, the effects of ionizing radiation are such that it changes the chemical composition and thereby the taste of the treated food. Medfly Infestation in oranges or in other fruit is also a problem, currently dealt with by the use of toxic gases.

The use of electric fields to destroy noxious biological organisms is a possible alternative. The principal benefit, if properly applied, would be the ridding of the material of the noxious organisms, while at the same time not significantly raising the temperature, incurring by-products of ionizing radiation, or causing the development of new chemicals of unknown effects.

Early investigators considered the use of radio frequency (1 MHz to 600 MHz) or microwave frequency (1 GHz to 10 GHz) electric fields to provide non-thermal electric field destruction of noxious organisms. However, past efforts employing these frequencies have not caught on. This is due, in part, to inappropriate equipment designs or poor biological science, or a combination of both. Where science has been rigorously adhered to, little or no disinfection or sterilization by radio frequency (RF) or microwave frequency has been observed. Part of the problem is that most of the research in these frequency regions has been done on the basis of available equipment, and not on the basis of a first principal which exploits "an undisputed kill mechanism". Furthermore, almost all test procedures and protocols which claim significant positive effects often resulted in considerable localized heating, thereby confusing thermal effects with the purely athermal electromagnetic effects.

For example, many attempts have been made to use electromagnetic energy, principally in the microwave or radio frequency range, to effect pasteurization, disinfection, or sterilization. A good summary of this past work appears in a book by Robert V. Decareau entitled "Microwaves in the Food Processing Industry", published by Academic Press, 1985. In this summary the conclusion is that the use of shortwave band or higher frequencies for the abovementioned purposes either does not occur or is not sufficiently reliable for food processing or other disinfection purposes.

Apart from the radio frequency and microwave regime, the bactericidal and possibly insecticidal effects of electric currents have been investigated by simply passing direct current or low frequency alternating current through the host product. Other applications considered the passage of low frequency current to create ohmic heating throughout the volume of the medium under treatment. Other methods have employed the use of high voltage arc discharges to create hydraulic shock waves.

Recently, and quite apart from the use of electric fields to rid host material of noxious biological organisms, several separate lines of investigation have clearly demonstrated non-thermal or "sure-kill" electric field effects. These studies are identified in the disclosure statement accompanying this application.

As such, the known "undisputed kill mechanisms" generally involve the application of a sufficiently large amplitude unipolar electric field intensity over an appropriate duration to biological organisms (such as bacteria) to irreversibly rupture cell wall membranes in the organisms. Experimental data demonstrates that this can be done by application of electric field intensities in the order of at least a few thousand to ten thousand volts per centimeter for the duration of at least 0.2 microseconds and preferably longer. Such enormous field intensities are very difficult to generate and apply by conventional equipment without arc-over or electrical breakdown. If not optimized, high power consumption could well result in temperature increases in the material being treated.

Thus, the "sure kill mechanism" depends on the application of a unipolar pulse of sufficient duration and amplitude to cause breakdown of the cell membranes. Such unipolar pulses are needed to cause a charge to build up across the membranes and when maintained at a sufficient amplitude, about 3000 v/cm or greater, and adequate duration, in the order of 0.2 microseconds and greater, will eventually cause the membrane to rupture or otherwise be disabled.

One investigation, for example, was a study to discover ways in which to improve the treatment of electrical burns experienced by power-line workers. In this study it was reported that two phenomena take place during electrical shock (assuming that fibrillation does not occur). These phenomena are cell degradation by the Joule heating and, second, by non-thermal cell-wall rupture effects of strong electric fields. In a study by Diane C. Gaylot ("Physical Mechanism of Cellular Injury in Electrical Trauma", Dr. of Philosophy dissertation at the Massachusetts Institute of Technology in September of 1989), she demonstrated that cell membrane disruption by electrical stress occurs and can lead to irreversible effects and ultimate destruction of the cells. She presents this as over a dozen references regarding the effects of intense electric fields which lead to irreversible breakdown of the cell.

Other investigators have used, as a standard laboratory technique, brief and yet intense electrical pulses that produce cell fusion or change genetic material. A review of this work with extensive references is given by Ulrich Zimmerman in "Electrical Breakdown Electropermeabilization and Electrofusion", Rev. Physiol. Biochem. Pharmacol., 105:176–256. A variety of electrode configurations are employed with the principal objective to effect reversible breakdown for cell fusion and genetic research.

Recently, in Dunn U.S. Pat. Nos. 4,695,472 and 4,838,154, methods and apparatus are described which utilize the membrane rupture effect to aid in the preservation of food products, particularly liquid food products such as milk, fruit juices and fluidized eggs. While apparatus such as described by Dunn is suitable for treating liquid foodstuffs in limited volumes, the method and apparatus is not suitable for the treatment of large volumes of material contaminated by noxious biological organisms because it may require unduly large amounts of energy, thereby rendering the process uneconomical. Furthermore, the electric field applicators described by Dunn are far from optimum and are prone to electrical breakdown, caused by the false assumption by Dunn that a uniform electric field represents the optimum way to present electrical breakdown. In the processes described by Dunn, uniform electric fields are created by parallel plates. However, during the application of very high intense electric fields to materials between the plates, some type of heterogeneity such as a gas bubble may occur which will create a region of excess electric field intensity or microplasma which rapidly propagates, via electron avalanching plasma effects, from one plate to the other, thereby causing a highly conducting plasma-like streamer which shorts out the two plates and the effect of the electric field, thereby negating the treatment process. As will be shown later, the use of such parallel plates to create uniform electric fields actually tends to defeat the purpose of the system and can lead to system instability unless the material being treated is ideally homogeneous.

Doevenspeck, in U.S. Pat. No. 3,265,605, shows a basic configuration which is less likely to develop streamers except in one region. This configuration consists of a short carbon rod coaxially located in a longer hollow metallic or carbon cylinder. However, excessively large electric field intensities are created in the region near the edges or exposed end of the solid cylinder or electrode in the treatment region, thereby forming microplasmas which can initiate streamers or arcovers. Furthermore, Doevenspeck does not address any type of optimization procedures and does not specify pulse widths or other parameters which lead to optimum and economical operation.

In U.S. Pat. No. 4,457,221, Geren describes sterilization apparatus designed for killing organisms in place within the host by means of successive, relatively long duration, high current density pulses of electricity of alternate polarity. The pulses are passed through the host and contaminating organisms for a period of a few seconds. The current is conveyed to the host from electrodes immersed, with the host, in a weak electrolyte. Geren proposes to use a pulse duration of 200 microseconds to 5 milliseconds, of successive alternate polarity with a current range of 50 milliamperes to 5 amperes per square centimeter, at a pulse rate between 100 and 1,000 times per second. In this instance, 200 microsecond pulses, repeated 200 times per second, are too long and too energy consuming in most practical situations involving high conductivity materials. Furthermore, the 5 amperes per square centimeter current density may not be sufficient to achieve the required sure kill electric field intensity at room temperatures. Methods to optimize the conductivity values for the "weak electrolyte" are not presented.

In U.S. Pat. No. 3,095,359, Heller proposes employing a frequency from 1 to 250 megacycles at voltages of up to 100 kilovolts with pulse widths ranging from 1 microsecond to 10 milliseconds at pulse repetition rates of 30 to 10,000 pulses per second. He also proposes exposing the microorganisms in a medium such as water, which is isolated from the electrodes via a thick sheet of dielectric material, such as plastic. However, the use of such plastic isolators, even though very thin, increases the source voltage requirements to impractical levels. Furthermore, Heller proposes to use sinusoidal waveforms which reverse the polarity, thereby reversing the charge distribution and negating the charge buildup across the membranes.

L. I. Markitanova, as reported in the Journal of Applied Chemistry of the U.S.S.R., Volume 59 (11)/pg 2, 1986, reports on the destruction of bacteria in treated waste waters by the application of direct current voltages across the cells. The voltage applied was of the order of 200 volts per centimeter and the dwell time was of the order of 25 seconds. Although bacteria were reported destroyed, this approach could result in a substantial temperature rise as well as inefficient use of electrical energy, especially for low resistivity liquids, as well as electrode erosion.

Thus, one of the keys to success in the application of the "sure kill mechanism" is to use either very high intensity unipolar pulses or sinusoidal waveforms of very low frequency, such that an electrical charge can build up and can be maintained and sustained over a sufficient period of time, thereby causing rupture of the membrane. A second key is to use pulses of the smallest possible duration to minimize energy consumption. The third and most important key is the use of an exposure system which is essentially immune to electrical breakdown effects.

To overcome the foregoing difficulties, this invention describes a method wherein the power consumption can be optimized by reducing the pulse width. Such a reduction is realized at the expense of increasing the amplitude of the applied pulses. However, such a pulse-width energy reduction process can be continued until the "sure kill" energy consumption requirements of the pulse abruptly increase. Such an increase occurs at approximately one microsecond, depending on the type of biological organism or entity to be destroyed. The requirement for increased field intensity leads to a second requirements that the field exciter must be highly immune to the generation of streamers or sparke discharges. As opposed to parallel plates, which create a uniform field, it can be demonstrated that a nonuniform field is more appropriate, a field distribution which inherently suppresses the development of short circuits or streamers. The optimum arrangement requires that the current density in the medium being treated be controlled, rather than the field intensity, and that the optimum electric field distribution is nonuniform rather than uniform. Also, the charge densities or Current densities on the electrodes or in the material being treated should not vary abruptly or vary greatly; those densities should not change significantly even though the dielectric properties of the media being treated may change, either locally or generally.

The above is analogous to supplying electric energy from either a constant voltage source or a constant current source to a resistive load whose resistance decreases with temperature as the load resistor heats up. If a constant voltage is applied to such a load, the tendency is for the load current to increase progressively, thereby increasing the dissipation of heat because, as the resistance of the load progressively decreases, the power dissipated increases as the product of the applied voltage and current. If the heat liberated in the load resistor is not rapidly removed, thermal runaway can occur, which leads to the destruction of the load resistor. On the other hand, if the load resistor is energized by a constant current source, any decrease in the load resistance due to temperature increase results in a lower dissipation because the power dissipation is proportional to the product of the resistance times the square of the current. Similarly, in the case of the controlled current density method, any decrease in the resistivity in any local volume of the material being treated due to a heterogeneity results in both reduced power dissipation and reduced electric field intensity. The local electric field intensity is controlled by the product of the current density (which is largely constant) and the resistivity (which decreases upon the onset of a streamer or arc). Thus, a controlled or constant current density applicator tends to snuff out incipient arcs at the outset. On the other hand, a uniform electric field applicator tends to induce a runaway streamer or arc, since the dissipated power progressively increases once an incipient arc is formed.

To treat solid material, it is necessary to encase the host material, particularly if it is all solid, by immersing it in a dielectric of similar value, such as in water or foam or some other type of fluid medium. If the material being treated is a relatively good or low loss dielectric, equipment to recover the energy stored in the applied field is also a necessary requirement to achieve optimum efficiency. Post-treatment techniques may also be needed, either to recycle the thermal energy in the treated material (if pre-heated) or to recycle various types of encasing dielectrics such as deionized water or conducting foam. Means to sense the electrical properties of the fluid media are necessary in order to apply the proper current densities.

SUMMARY OF THE INVENTION

It is the principal object of this invention to provide novel methods, processes and apparatus for the energy efficient destruction of noxious biological organisms, especially for destruction of noxious biological organisms in large volumes of fluids or solids.

A principal object is to provide novel or optimized electric field applicators, which suppress electrical breakdown, in a system for destroying noxious biological organisms. Such applicators embody special and novel geometries and surface treatments so as to exhibit controlled current densities (rather than uniform electric fields) in the vicinity of or within the media being treated.

Another object of this invention is to define an optimum pulse width and amplitude wherein minimum energy consumption is realized, in a system for destroying noxious biological organisms.

Another object is to describe equipment and apparatus necessary to realize minimum energy consumption by recovering the energy that otherwise might be wasted in the exposure process, in a system for destroying noxious biological organisms.

Another object is to describe a simple method of preventing electrolytic erosion of the electrodes during high pulse level exposure, in a system for destroying noxious biological organisms.

Another object is to define the properties of dielectric fluids needed to encase solid materials during high electric field exposures such that small heterogeneities are mitigated and that related electrical breakdowns are avoided, in a system for destroying noxious biological organisms.

Another object is to describe a process control system where electrical properties of the fluids being treated or encasing the solids are sensed in order to apply the proper current density and/or to control the electrical properties of the fluid such that the required electric field intensity is applied.

Accordingly, the invention relates to an energy-efficient electromagnetic method for elimination of noxious biological organisms comprising the steps of:
  (a) conveying a material contaminated with noxious biological organisms into and through an exposure chamber;
  (b) in the exposure chamber, exposing the contaminated material to a nonuniform, high intensity electric field; and
  (c) in the exposure chamber, suppressing excessive current flow in localized regions, including suppressing arcing and current streamers;

the amplitude of the current density and electric field within the exposure chamber being controlled, in accordance with the conductivity and/or dielectric constant of the contaminated material, so that the electric field intensity is of the order of 3,000 volts/centimeter or more.

DEFINITIONS

For purposes of this patent application, the term "noxious biological organisms" is defined to include insects and related eggs or larvae, animal parasites in various forms, small animal pests in various forms, fungus, microorganisms such as mold and related forms, bacteria and related forms, and possibly some viruses.

Also for the purpose of this application, various materials are defined in terms of permittivity, which is a complex wherein $$\epsilon = \epsilon' - j\epsilon'' \quad (1)$$

where $\epsilon$ is the permittivity $\epsilon'$ is the real component of the above, and $\epsilon''$ is the imaginary component of the above $\epsilon'$ is often taken as the dielectric constant and is related to the relative dielectric constant $\epsilon_r$ as follows: $\epsilon_r = \epsilon'/\epsilon_0$, where $\epsilon_0$ is the permittivity of free space. $\epsilon''$ is a measure of the conductivity of the media and is related to the conductivity o of the media and the dielectric constant as follows:

$$\frac{\epsilon''}{\epsilon'} = \frac{\sigma}{\omega\epsilon'} = \tan\Delta \quad (2)$$

where $\sigma$ is the conductivity at the frequency $\omega/2\pi$
$\omega$ is $2\pi f$
f is the frequency, and
tan $\Delta$ is the loss tangent.

The electrical field "E" and the current density "J" in a dielectric media are related as follows:

$$J = j\omega(\epsilon' - j\epsilon'')E \quad (3)$$

$$J = j\omega\epsilon'[1 - j\sigma/\omega\epsilon']E \quad (4)$$

$$J = [\sigma + j\omega\epsilon']E = yE \quad (5)$$

where $\sigma + j\omega\epsilon'$ is defined as the specific admittance "y", and $j\omega\epsilon'$ is defined as the specific susceptance.

All metals are viewed as perfect conductors and, in the case of other solids or fluids, where tan a $\Delta > 1$, the material is viewed as a lossy dielectric and where tan a $\Delta < 1$, the material is viewed as an imperfect dielectric.

DESCRIPTION OF THE PREFERRED EMBODIMENTS

Figure 1:
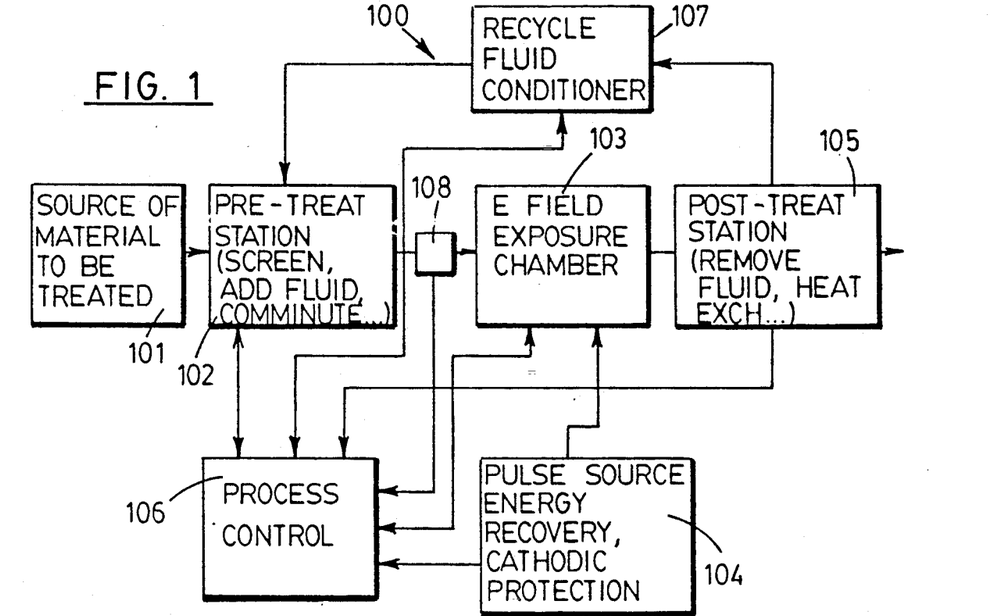
FIG. 1 is a functional block diagram of the invention which illustrates various steps in the process.

FIG. 1 illustrates the elements of a sterilization, disinfection, pasteurization, insecticidal or biocidal system 100. It consists of eight functional elements as follows; a source 101 of a material to be treated, a pretreatment station 102, an E field exposure chamber 103, an electric energy source 104, a post-processing chamber 105, a process control circuit 106, a recycle fluid conditioner 107, and one or more sensors 108 to determine the specific admittance of the fluids or materials.

The materials which can be treated by this system include various types of liquids such as waste water, swimming pool water, sewage, milk, and fruit Juices; semi-liquid food products such as baby food; solids such as oranges and grapes with insect infestations; meats or fish infected with parasites; pharmaceuticals, either in liquid or powder form; granular foods such as grain or flour; textiles such as garments, gauze and bandages; and wastes such as infectious hospital wastes.

The pretreatment function in station 102 may include comminuting or shredding of an incoming solid-like material from source 101 which, although initially non-homogeneous, becomes homogeneous on a gross scale. For solid objects, the contrast in specific admittance is reduced by adding distilled water, saline water or conducting foams, in station 102, selected so as to match the specific admittance of the solid material being treated. If the material to be treated contains large-sized objects such as found in infectious hospital waste, this waste is shredded to reduce the size of the particles to a size that can easily pass through the E field exposure chamber 103. In addition, to prevent arc-over and mitigate the contrast in the specific admittance, comminuted infectious waste being treated is mixed with a highly conducting foam. Some preheating may be needed, because it has been demonstrated that raising the temperature to approximately 60° C. enhances the electric field athermal killing effects and also assures destruction of the viruses in chamber 103. Preheating, when used, also occurs in station 102.

The electric field exposure chamber 103 is a key element in the operation of the system 100. The principal features of the chamber are such that the desired high intensity exposure can take place without either arc-over or development of streamers which, in effect, short out the electric field. The post-treatment station 105 includes heat recycling of fluids, assuming that the input material has been heated or cooled. If conducting foam or water has been used, station 105 may include provisions for the removal of the foam or the conducting water.

The electric energy source 104 may be a source of high voltage pulses of appropriate duration; those pulses are used to develop the required current densities and resultant electric fields in the exposure chamber 103. Two types of sources are most frequently employed. Thus, when the material to be treated within the exposure chamber 103 is a lossy dielectric with a conductivity in the order of $10^{-3}$ mhos or greater, most of the energy which is supplied to the E field exposure chamber is dissipated in the material as an ohmic heating. However, such dissipation, by the techniques noted here, can be made small, thereby limiting the temperature rise and the energy consumption. On the other hand, some of the material to be exposed and treated in chamber 103 may be an imperfect dielectric of low conductivity, such as pharmaceuticals, animal food grains, oils and gases. To obtain minimum power consumption with such materials it is desirable to recover the energy stored in the fields in the exposure chamber, since this energy is not otherwise dissipated. Special circuits to do this are described. In addition, for high conductivity fluids, cathodic protection must also be applied to prevent erosion of the electrodes via the direct-current component of the unipolar pulses. The electric energy source 104, as an alternative, may also generate low frequency sinusoidal waves of sufficient amplitude and duration, should this be the more appropriate efficient energy recovery source system.

The process control system 106 controls the various steps, either manually by proper displays of information, or automatically, depending on the process. This control system, utilizing information from sensor 108, controls the product of the specific admittance and current density such that the required electric field intensity is applied. This may be done either by varying the properties of the fluids or by varying the output of the fluid source 107.

Figures 2A, 2B:
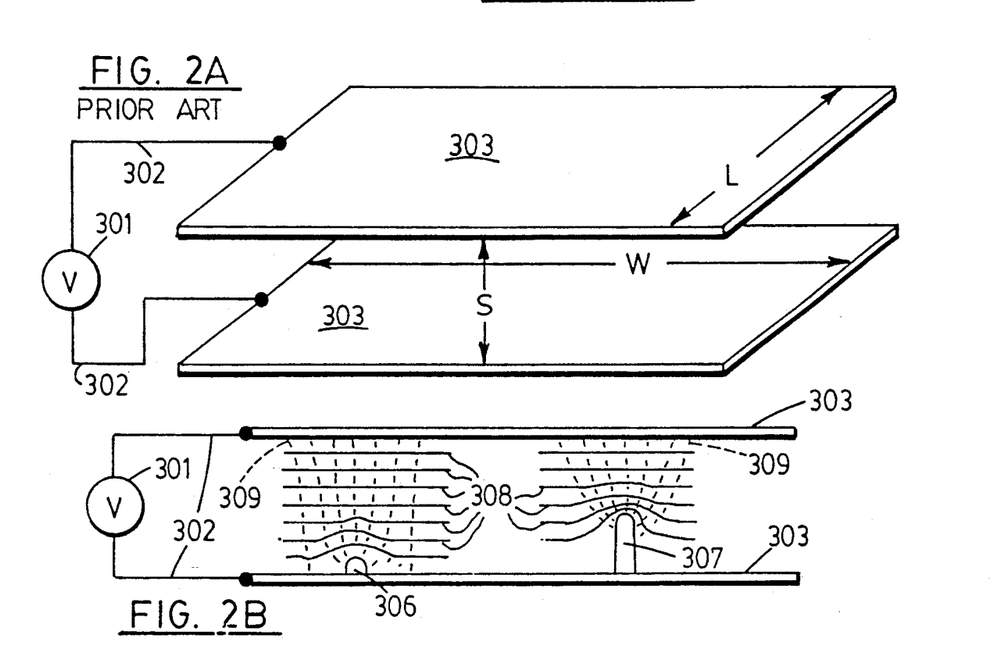
FIG. 2A illustrates a typical arrangement of parallel conducting sheets used in the prior art to generate uniform electric fields.
FIG. 2B illustrates changes in the equi-potential lines and current flow lines in the event of a heterogeneity in the parallel plate apparatus of FIG. 2A.

The most critical element in system 100, FIG. 1, is the exposure chamber 103. Prior to describing the improved exposure chambers of the present invention, a review on the deficiencies of prior exposure chambers is appropriate. Dunn, in U.S. Pat. No. 4,838,154, stated that the presence of excessively conducting, plasma-like streamers or arcs in the media could occur and that this could be remedied by the use of uniform electric fields which are created by parallel conducting plates, as illustrated in FIGS. 2A and 28. However, as stated by Dunn, the use of uniform fields does not prevent the formation of streamers, particularly when the medium passing between the plates is slightly heterogeneous. As will be shown, the parallel plate arrangement of Dunn tends to aggravate the development of streamers or arcs in liquids.

For example, consider FIG. 2A. In FIG. 2A a pulse source 301, is connected to two parallel plates 303 by conductors 302. The width W and the length L of each plate are large compared with the plate separation S. When a voltage is impressed on plates 303 from source 301, equi-potential lines 308 are generated, as shown in FIG. 2B. Displacement currents or conduction currents are shown as dashed lines 309. Now assume that a small heterogeneity 306 exists on or adjacent to the lowermost plate 303. This inhomogeneity 306, if more conductive than the other material between plates 303, will cause a disruption in the uniformity of the equi-potential lines 308, as shown near the nonhomogeneity 306. This results in a high concentration of conduction currents 309 near the tip of the heterogeneity 307. As a consequence, the equi-potential lines 308 are compacted around the tip of the inhomogeneity, resulting in an increased electric field intensity at the tip. This increased electric field, if sufficiently high, tears the electrons away from the molecules in the inhomogeneity 306, thereby creating additional electrons. These impinge upon other molecules, creating an avalanching effect of electrons which eventually create a conducting plasma or streamer. Such a conducting plasma would be contained if, as it grows, it enters into a region or condition of decreasing electric fields. However, because of the constant voltage applied to the electrodes 303, this plasma arc will tend to grow and encounter at its tip increasingly higher electric field intensities, thus enhancing its rate of growth as illustrated by the larger heterogeneity 307. Here it is seen that the average electric field intensity between the tip of the inhomogeneity 307 and the upper plate 303 has been doubled nd that the electric field in the immediate vicinity of the tip of the nonhomogeneity 307 is probably increased by a factor of thirty to forty. As a result, this enhances the propensity to form streamers and arcs between plates 303. Thus, Dunn's arrangement includes a major difficulty in achieving high electric field intensities wherein the parallel plate method is used to achieve uniform electric fields.

Figure 3A:
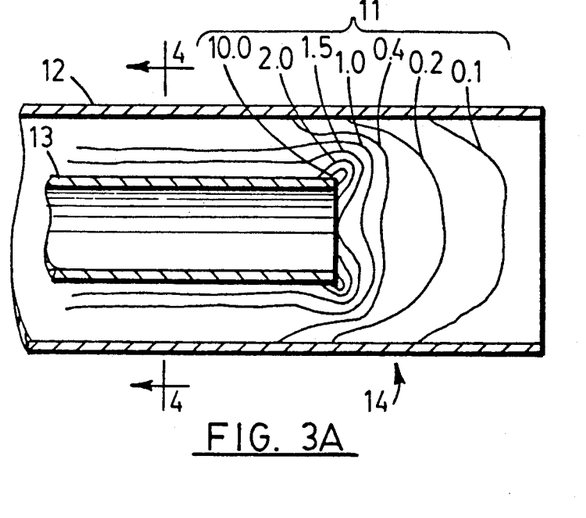
FIGS. 3A and 3B illustrate a prior art system in which the electrodes are formed by two concentric tubes, one of which is smaller in diameter and shorter in length than the other; this arrangement illustrates the unwanted electric field en
Figure 3B:
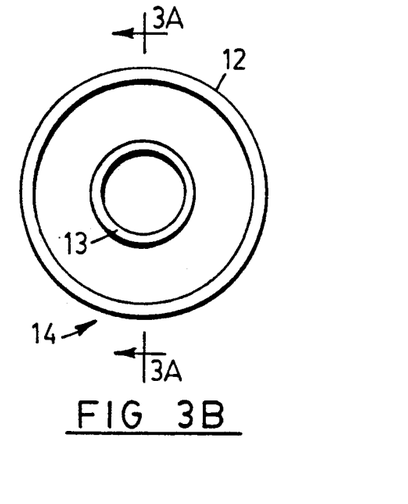

Another difficulty with the past art is illustrated by the electrode arrangement employed by Doevenspeck. Doevenspeck uses an arrangement 14 of coaxial, cylindrical electrodes like that shown in FIGS. 3A and 3B. The outer electrode 12 is hollow and encompasses but is spaced from a shorter inner electrodes 13. The space between the electrodes is filled with the material to be treated, and there is an electrical potential between the outer electrode 12 and the inner electrode 13. Shown in FIG. 3A are lines 11 of equal electric field intensity. It is seen that the electric field intensity peaks near the abrupt corners of the inner electrode 13. This occurs because electrons tend to repel each other and therefore are concentrated at the far reaches of a conductor, particularly near its corners and edges. As a consequence, because of the increased charge density, the accompanying electric field intensity is also increased. The enhanced electric field intensity at the corners can be a source of arc-over problems with the Doevenspeck arrangement if operated near the maximum electric field intensities.

Figure 4:
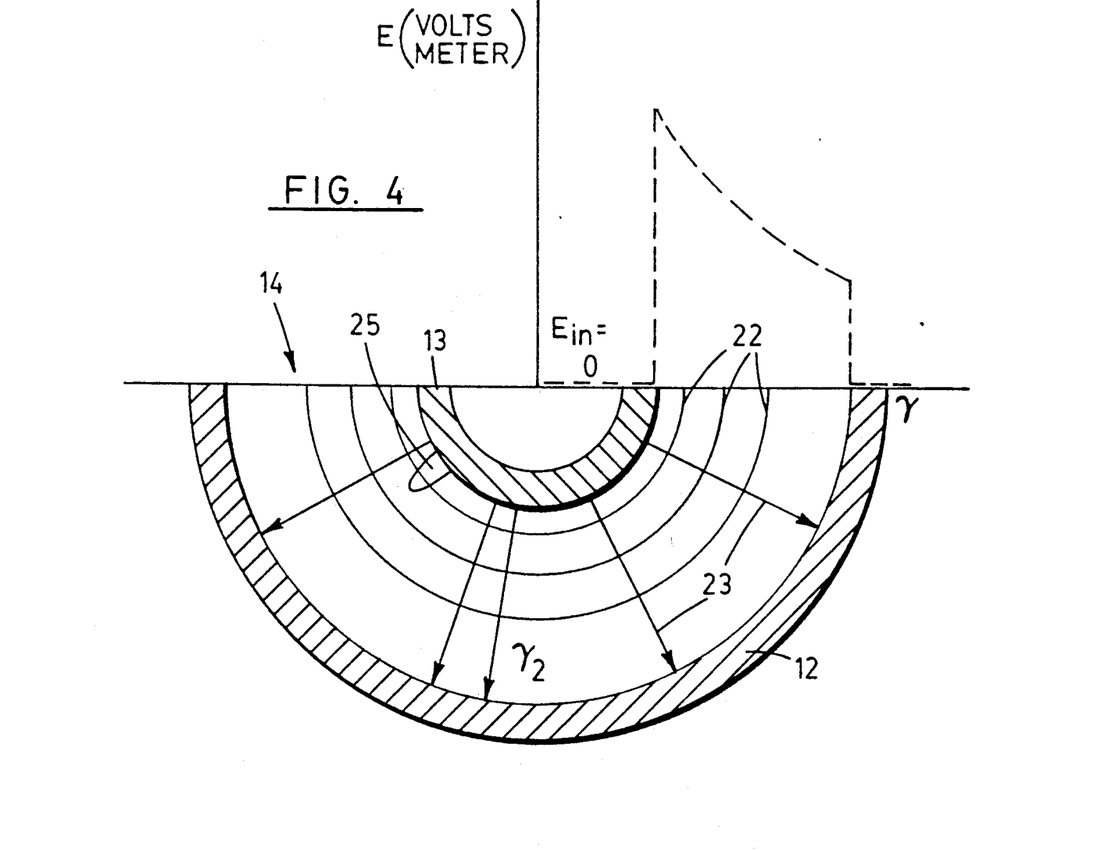

However, the Doevenspeck arrangement of coaxial cylinders offers a possible solution if designed properly. FIG. 4 shows a cross-section of the lower half of the coaxial arrangement shown in FIG. 3A with the cross-section taken at the plane 4—4. The lower half of FIG. 4 shows the equipotential lines 22 along with the conduction or displacement current lines 23. The outer conductor 12 is placed at a different potential than the inner conductor 13. The upper right-hand part of FIG. 4 is a plot of the electric field intensity. This indicates an electric field intensity of zero on the inside of the inner conductor 13 which rises to a peak value at the surface of the inner conductor 13 facing the outer conductor 12. The field intensity $E_r$ declines gracefully to a smaller value at the inner surface of the outer conductor and falls to zero inside of the outer conductor and beyond.

Such a divergent field intensity arrangement, which falls off gradually, is advantageous to suppress streaming effects. For example, consider an inhomogeneity 25 on the inner conductor 13 which is the most likely since this location has the highest electric field intensity. As this heterogeneity grows, it enters into regions of decreasing electric field intensity. As a consequence, the tendency for the arc and streamer to grow and form a complete short circuit between the inner and outer conductor is thereby suppressed. Furthermore, it can be shown that the admittance or impedance between concentric tubes varies only as the logarithm of the ratio $(r_2/r_1)$ of the outer radius to inner radius $(r_1)$. Thus, if the inhomogeneity 25 were extended circumferentially such that, in effect r was increased, such an increase would have only a small effect on the impedance. And, since the impedance (along with the applied voltage) controls the current flow between the electrodes, the effect on the current density is also small.

Figure 5:
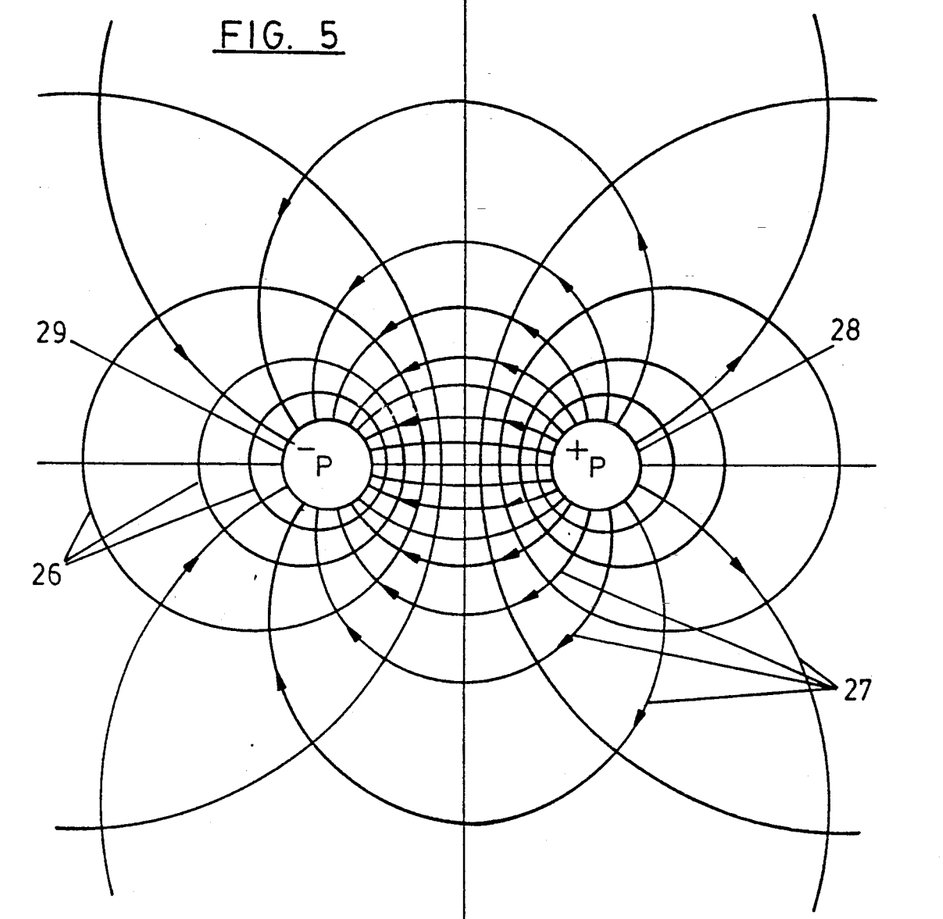

Similar divergent fields which are capable of suppressing the growth of streamers or short circuiting arcs can also be realized by isolated cylindrical conductors or pairs of cylindrical conductors as illustrated in FIG. 5. This illustrates a transverse cross-section of two parallel conducting cylinders 28 and 29 which are oppositely charged. The equi-potential lines for this construction are shown at 26 and the lines of displacement-or conduction current flow, depending on the media in which the parallel conductors are inserted, appear at 27.

Note that the electric field is highly divergent and that, if the media is held in the immediate vicinity of either conductor, any tendency for a streamer to form is suppressed because the streamer enters into regions of decreasing field intensity.

Figure 6:
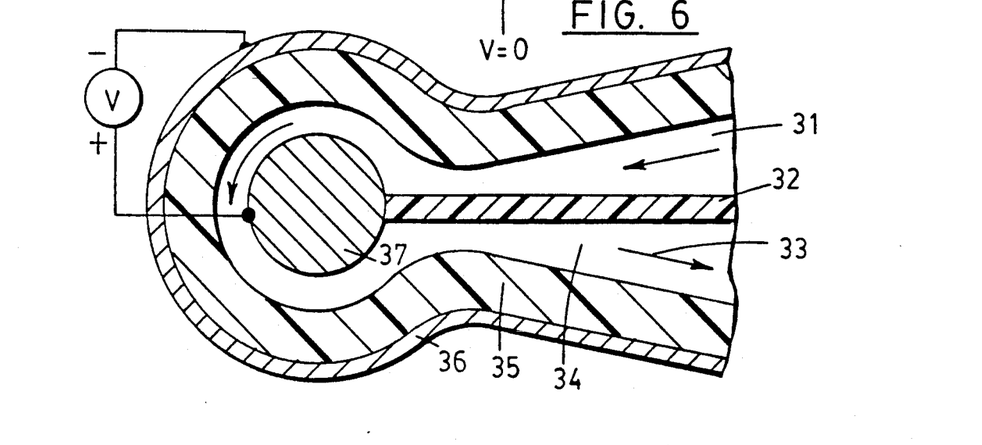

Divergent field streamer suppression can be enhanced by treating the surfaces of the electrodes. This is illustrated in FIG. 6. A cross-section of two coaxial conducting cylinders in which the inner conductor 37 is charged positive respect to the outer conductor 36. Fluids to be treated enters in the direction 31 into the processing area and flow around the immediate vicinity of the inner conductor 37. The fluids are restrained from the immediate vicinity of the outer conductor 36 by means of a material 35 which has a specific admittance similar to or less than that of the fluids being treated. 34 shows the plenum region from which the treated fluids exit in the direction arrow 33. A septum 32 between the ingressing and egressing fluids is made from an insulating material.

Figures 7, 8:
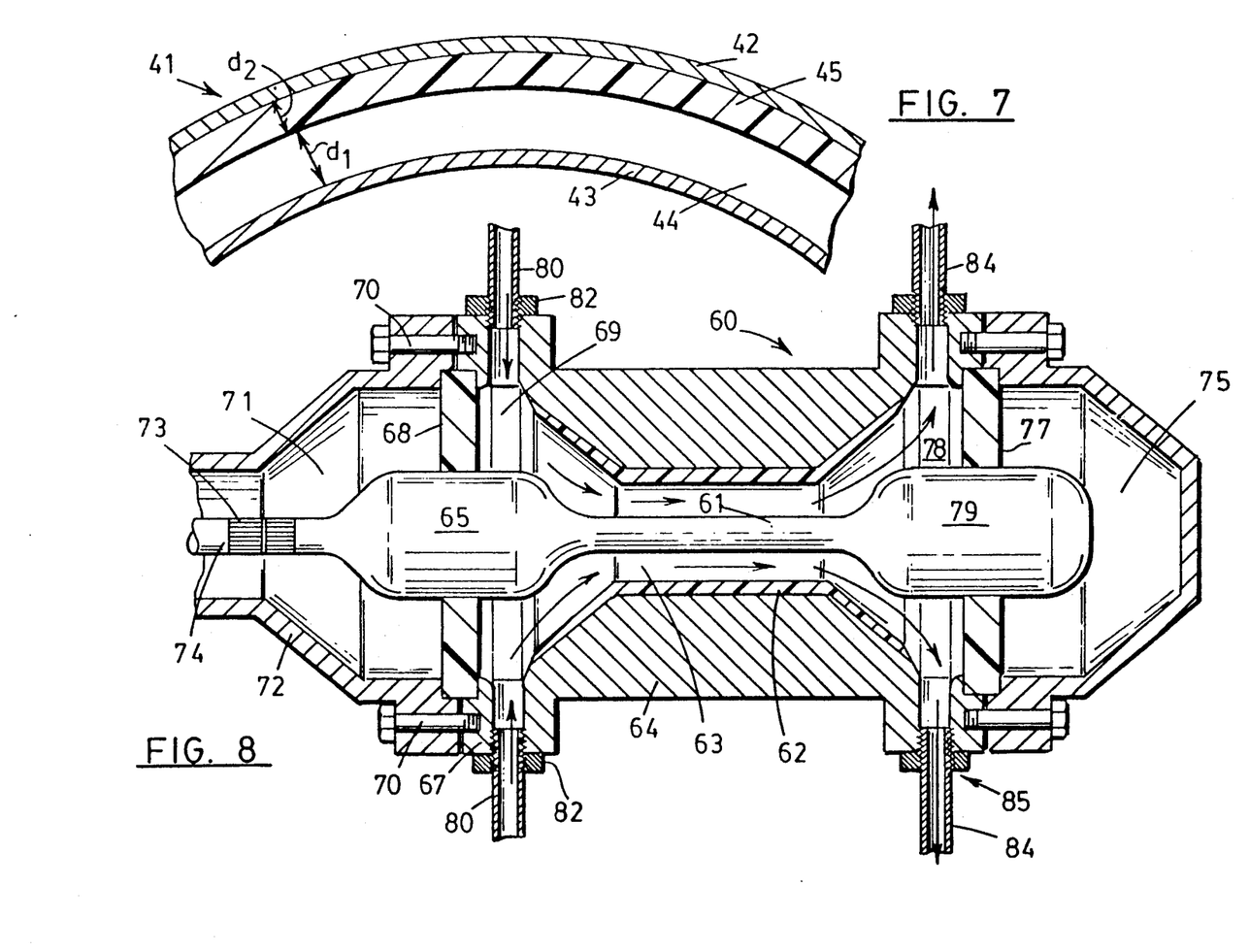

FIG. 7 illustrates another arc and streamer suppression capability by the use of a properly chosen dielectric coating. A section 41 from a field inducing structure shows an outer electrode 42 and an inner-electrode 43. A medium 44, which has a specific admittance $y_1$, is being treated; the fluid medium 44 constrained by a wall of isolation material 45 which has a specific admittance $Y_2$. The media region has a thickness d and the isolation material has a thickness $d_2$. Assuming that the two materials are both lossy dielectrics, with $\sigma_1 >> \omega\epsilon$, and $\sigma_2 >> \omega\epsilon_2$, the current density which flows between the electrodes 42 and 43 is determined approximately by:

$$J = \frac{V(\sigma_1 \sigma_2 d_1 d_2)}{(\sigma_1 d_2 + \sigma_2 d_1)} \quad (6)$$

where V is the voltage applied between the electrodes 42 and 43.

If the specific admittance (that is $\sigma_2$) of the isolation material 45 is chosen to be substantially less than specific admittance (that is $\sigma_1$) of the material 44 being treated, so that $d_1/\sigma_1 < d_2/\sigma_2$, equation (6) becomes $$J = \frac{V \sigma_2}{d_2} \quad (7)$$

Furthermore, the electric field at electrode 42 is given by $J/\sigma_2 d_2$ and at electrode 43 is $J/\sigma_1 d_1$. Except for the trivial case of $\sigma_2 d_2 = \sigma_1 d_1$, the electric fields normal to the surfaces of 43 and 44 will be different, even if the electrodes 43 and 42 are nearly parallel plates.

Under the above conditions, the current density becomes largely independent of the conductivity of the medium 44 being treated. Thus, if a small heterogeneity occurs and induces a small region of electron avalanching, the conductivity of the region increases; but, under constant current density conditions, an increase in conductivity results in a reduced voltage drop across the heterogeneity, thereby suppressing the streamer or arc.

The advantages of the systems shown in FIGS. 6 and 7 are that if an inhomogeneity causes a streamer to form it is quickly suppressed, either because the fields are diverging or because of constant current density. This assumes the electrical breakdown characteristics of the dielectric materials 35 in FIG. 6 and 45 in FIG. 7 are greater than that of the fluid being treated.

When the material to be treated is highly conductive, the dielectric properties of the isolation material which constrain fluids being treated should also be conductive. Such conductive material may be formed by embedding finely divided particles of silver in a rubber-like silicon plastic material wherein ohmic conduction is formed by random contact between the particles which are partially isolated by the silicon material. For lower conductivity material, various types of conducting plastics are available, such as carbon loaded plastics or plastics filled with conducting fibers.

The dielectric isolation material (e.g. 35 in FIG. 6, 45 in FIG. 7) might also be a liquid, such as partially deionized water, which has a controlled conductivity. In this case, an ion permeable membrane which is unaffected by the passage of electrical currents is used to isolate the media. If the conductivity of the isolation region is to be maintained is different than that of the fluid or media being treated, a low voltage direct current potential may be required to suppress the flow of ions into the lower conductivity medium. For fluids which are poor dielectrics with very low conductivity, the selection of the properties of the dielectric isolating material 35 or 45 is much easier. Typically, most nonconducting oils have dielectric constants of ten or less and finding materials with dielectric constants of ten or less is easily accomplished.

Instead of the circumvential flow illustrated in FIG. 6, an axial flow treatment system 60 is shown in FIG. 8. The treatment system 60 is comprised of two coaxial conductive cylinders, an inner cylinder 61 and an outer cylinder 64. The outer conductor 64 is shown as coated with material 62 to suppress breakdown. The fluid to be treated flows through the space 63 between the inner conductor 61 and outer conductor 64. Near the axial extremities of the treatment volume or chamber, the inner conductor 61 is enlarged to reduce the surface field intensity. The enlarged portion 65 of the inner conductor passes through an insulating disk 68 which carries the inner conductor into a transition section 71 which is preferably filled with a high pressure inert gas to prevent electrical breakdown. An inner connecting bullet arrangement 73 connects the outer portions of the inner conductor 65 with the inner conductor 74 of a coaxial cable which supplies pulse power to the system. A backshell 72 is fastened to the outer portion of the outer conductor 67 by means of screws 70. Similarly, on the right-hand side, the inner conductor 61 again is enlarged, at 79, as it emerges from the treatment area into the plenum area 78. An insulating disk 77 serves the same purpose as disk 68 in the left portion. The transition section 75 is preferably filled with an inert gas which leads to a terminating system, not shown. The terminating system may include the means to suppress arc development due to the presence of high voltage fields on the inner conductor.

The fluids to be treated enter into the left-hand plenum area 69 via a plurality of tubes 80 each attached by a nut 82. The fluids enter the left plenum area 69, and progress longitudinally to the right, as seen in FIG. 8. The processed fluids are extracted by a manifold system. The manifold systems comprising a plurality of tubes 80 or 84 enter or extract the fluids is not entirely shown. The coaxial cable system for connecting a pulse source to the conductors 61 and 64 is not fully shown, nor is the high voltage terminating system to prevent capacitive discharge from the inner conductor. To prevent streaming or arc-over in the system, the use of uniform electric field criterion is replaced by assuring that the charge distribution or current density is reasonably uniform and does not have any noticeable discontinuities. Since the electric field at the surface is directly proportional to the charge distribution, this assures that the design of the system will be such that it will not have the field enhancement features shown in FIG. 3. To prevent the development of streamers, the charge distribution on one electrode should be somewhat less than the other electrode. Typically, for the system shown in FIG. 8, the charge distribution should be at least 10% different than on the opposite electrode. To prevent excess charge distribution peaking, the radii of curvature of the different portions in the high intensity field portion of the treatment chamber 60 should be comparable to or greater than that of the radius of the inner conductor 61. In regions 69 and 78 of the plenum chambers, radii that are as little as one-third of the inner conductor could be tolerated in the low field intensity regions.

The field exposure chambers shown in FIGS. 4, 5, 6, and 7 can be used for a variety of fluids, either liquid or gaseous. That shown in FIG. 8 can also handle semi-fluids such as baby food or other thick liquids which are either conducting or non-conducting.

Figures 9, 10:
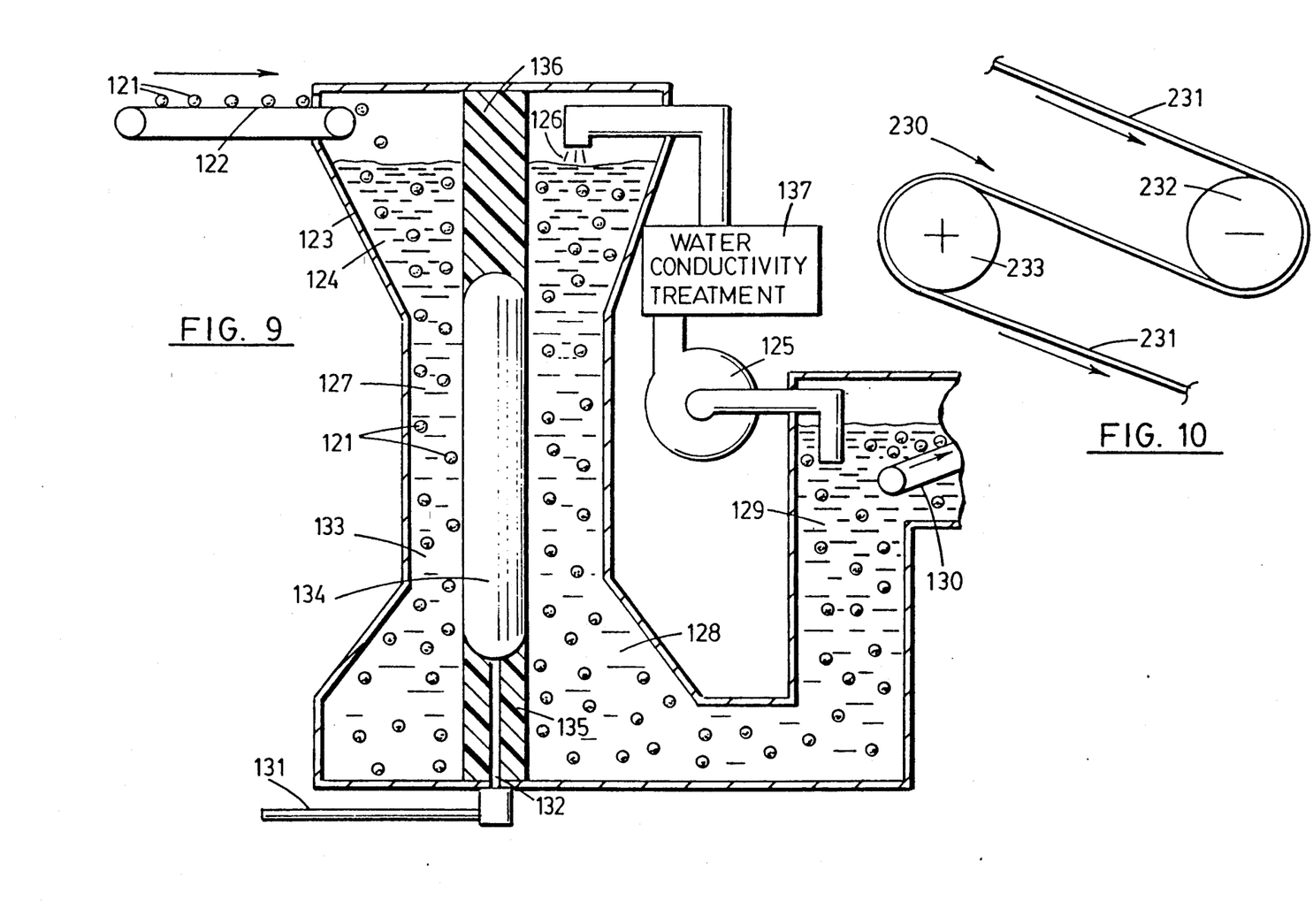

When solid material is to be treated, such as oranges which have a Medfly egg or insect infestation, the arrangement shown in FIG. 9 may be employed. The treatment system 120 transports oranges 121 on a conveyor belt 122 to be dumped into the water in an upper plenum 123. The oranges are then pulled down by means of the pumping action of a pump 125 which carries the water back to a discharge point 126, thereby causing, in the reaction chamber 127, a rapid downward flow which carries the oranges past the treatment chamber, into a lower plenum 128, and into a final discharge area 129. Then the oranges are removed on a belt conveyor 130.

High intensity pulses are supplied by the cable system 131 from a pulse source (not shown). Each pulse enters the treatment chamber via another coaxial cable system 132 which is embedded in an insulating plastic 135 such as a tetra fluoroethylene plastic. The inner conductor of the coaxial cable 132 is connected to an inner treatment conductor or electrode 134 to develop a potential, and an electric field, between the inner conductor 134 and the metal of the outer conductive wall 133 of the treatment chamber 120. Insulating material 135 is employed to isolate the coaxial cable 132 and to provide spark-over resistance to the rounded end of the inner conductor 134. An insulation tube 136 over the top of the inner conductor 134 is also supplied to position the inner conductor and to provide arc-over protection from the high field intensity which accumulates near the ends. A water treatment system 137 controls the conductivity of the water by means of a sensor system (not shown), which controls a salinity additive or a de-ionizing function so as to obtain the proper conductivity for the water in the system of chamber 120. The principal dielectric parameter, in this case the conductivity of the oranges, is matched insofar as possible by the conductivity of the water.

Another arrangement 230 for treating materials such as cloth, thin films or medical textiles is shown in FIG. 10. In this case, two parallel cylinders 233 and 232 are charged oppositely. The cloth or fabric 231 to be treated is passed in an S-type loop around the cylinders, which are periodically pulsed or excited to effect the treatment. Not shown are the source for the cloth entering into the treatment area and also the roller system to collect the treated cloth.

In the case of infectious hospital wastes, these are first shredded and then comminuted such that the particles are of a relatively small size. After comminution these are then immersed in foam which then enters into a treatment chamber, which may be similar to the chambers shown in FIGS. 8 and g, except the entrance to the plenum will be enlarged. Field excitation is then applied between the electrodes, initially to heat the material to approximately 60° C. This assures that viruses will be disabled and further enhances the kill effectiveness of the electric field. Next, additional hot 60° C. foam is added and mixed with the shredded waste which in turn is injected into the high intensity field treatment chamber and exposed to the required current density waveforms. The combination of the heating plus the electric field should accomplish significant disinfection or complete sterilization. In this case, since heating to 60° C. is desirable, the use of 300 kHz sinewave excitation would be appropriate to both heat and to effect electric field kill.

In the case of waste water and sewage systems, water is passed through a system similar to that shown in FIG. 8. Prior to the entrance into the treatment area, water screens are placed to eliminate major heterogeneities. The water may be heated to assist in the disinfection process. After treatment, a heat exchanger may be used to recycle a portion of the heat in the system.

When large volumes of material are to be treated, the energy usage for the athermic treatment of the material must be considered. This includes the energy dissipated within the material itself and the energy consumed in the treatment equipment. Also, if the energy liberated in the material is too high, then the temperature of the treated material might rise to an unacceptable level. The energy liberated in the material is proportional to the following:

$$J = \sigma E_i^2 TN \tag{8}$$

where:
$\sigma$ is the conductivity of the material
$E_i$ is the rms value of the electric field
$T$ is the duration of the pulse
$N$ is the number of pulses
$J$ is the joule energy expended in the material
The temperature rise within the material is given by:

$$\Delta C = \frac{J}{(\text{specific heat})(\text{weight})} = \left( \frac{\sigma E_1^2 TN}{(\text{specific heat})(\text{weight})} \right) \tag{9}$$

$$J_{max} = [(\Delta C)_{max}](\text{specific heat})(\text{weight}) \tag{10}$$

The maximum allowable energy $J_{max}$ is governed by the maximum allowable temperature rise, $(\Delta D)_{max}$.

Figures 11A, 11B, 12:
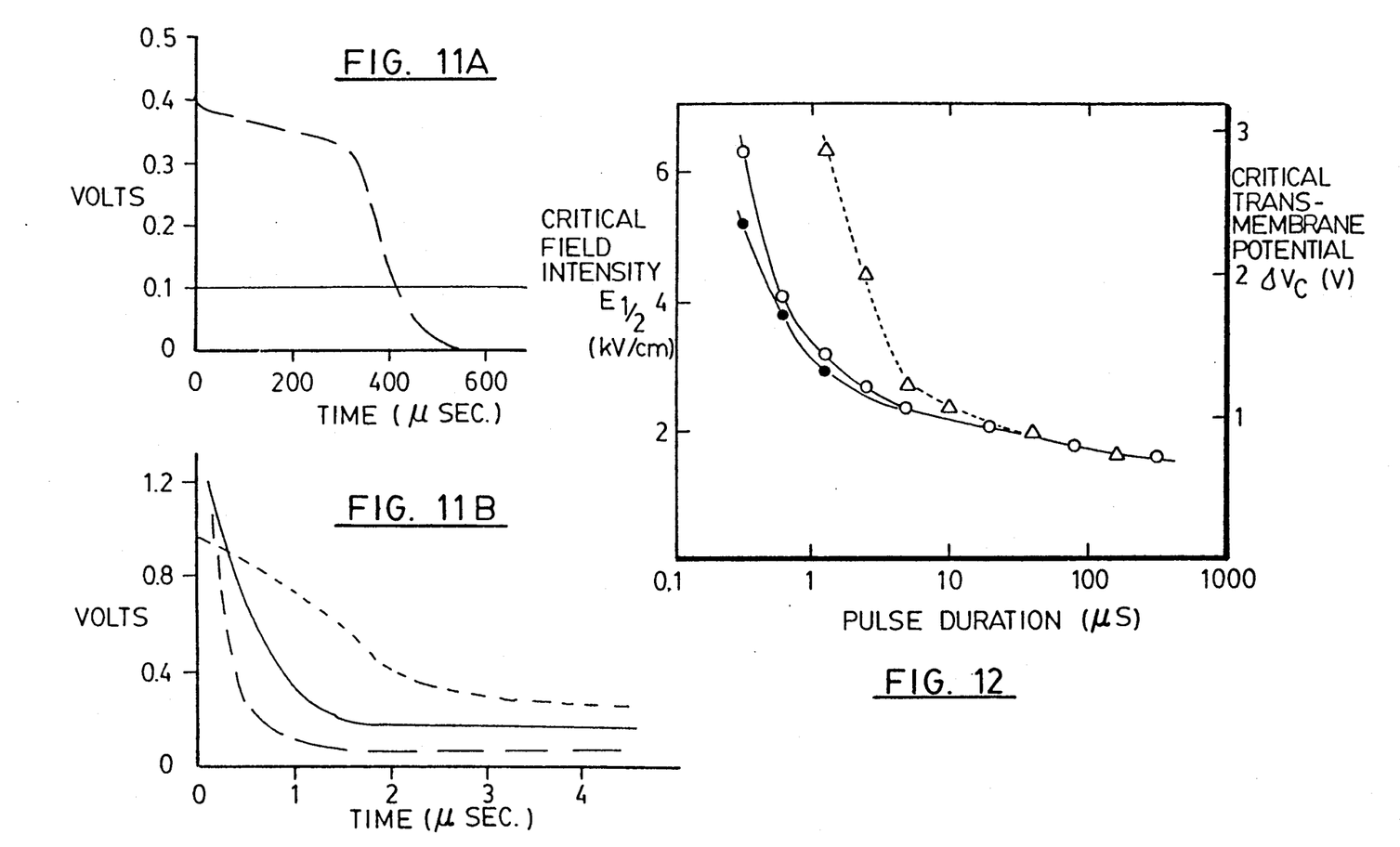

To determine the optimum parameters for minimum energy consumption while at the same time achieving destruction of cells, a review of established cell destruction mechanisms is noted. FIGS. 11A and 11B (Zimmerman, et al., "Cells with manipulated functions: New perspectives for cell biology, medicine and technology." Angew. Chem. Int. Ed. Engl., 20:325-344, (1981) show what happens when different values of charge are placed across a single membrane. When charged to 0.1 volts for 500 microseconds (see FIG. 11A), no effect is noted. When charging to 0.4 volts for 400 microseconds, an irreversible breakdown results.

FIG. 11 also illustrates the amplitude and frequency dependent nature of the phenomena. For example, if a charge which created 0.4 volts was applied, as in FIG. 11A, it is seen that if the polarity of this charge were reversed prior to about 400 microseconds, the destructive processes could well be avoided. Such a non-kill charge reversal within this time regime could be illustrated by applying electric field intensities of a sinusoidal nature which had frequencies above about 3,000 Hz. Other data shows that if the charge were sufficient to develop 1.2 volts, the killing effect could be avoided only if the polarity was reversed at a rate greater than about 1 MHz.

The above may explain why very few athermal nonionizing effects have been observed, since many of the past tests have been designed to investigate athermal effects and have employed frequencies greater than 10 MHz. From this we conclude that a unipolar or single polarity pulse exposure is better than a sinusoidal exposure if the membrane damage phenomena is to be exploited for sterilization, insecticidal or bactericidal purposes. An exception is if the frequency of the sinusoidal exposure is less than about 1 MHz.

FIG. 12 (Kinosita, "Formation and resealing of pores of controlled sizes in human erythrocyte membrane." Nature, 268, 4:438-440, (1977) presents the membrane potential or critical electric field intensity to cause hemolysis as a function of the duration of the applied electric field intensity. From this data we can determine the optimum pulse width based on the employment of Equation (8).

Figure 13:
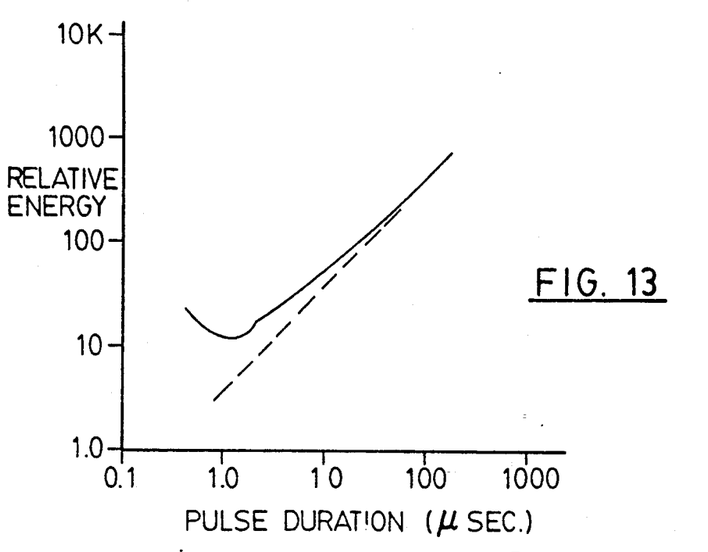
FIG. 13 illustrates the relative energy required to cause irreversible membrane breakdown as a function of pulse duration based on the required critical electrical field intensity shown in FIG. 12.

Using Equation (8) and the data of FIG. 12, the relative energy as a function of pulse duration is plotted in FIG. 13 as a solid line 250 for an initial probable-kill charge voltage of 1.2 volts. For a no-kill initial charge voltage of 0.4 volts, the dash line 251 is also presented, which indicates for time durations shown that little or no degradation of the cell membrane occurs. Note that the minimum energy occurs around about 1 microsecond for this example.

Other researchers have demonstrated that non-destructive breakdown can occur for potentials in the order of 500 millivolts and for pulse durations in the nanosecond into the microsecond regime. This indicates that some effects may occur at shorter pulse durations, but only if the electric field intensity is considerably higher.

Figure 14A:
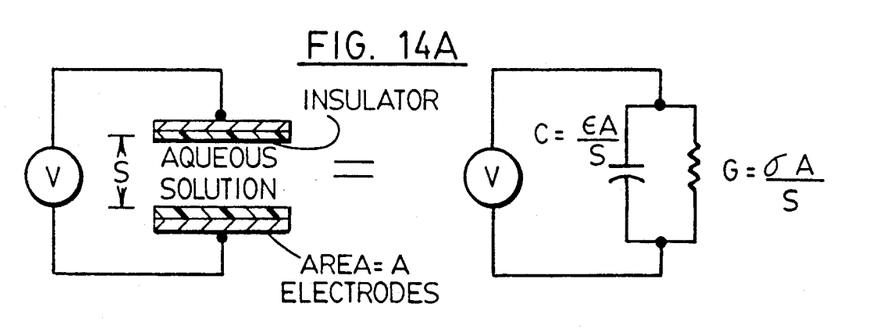
FIGS. 14A and 14B illustrate equivalent electrical circuits for two different treatment arrangements.
Figure 14B:
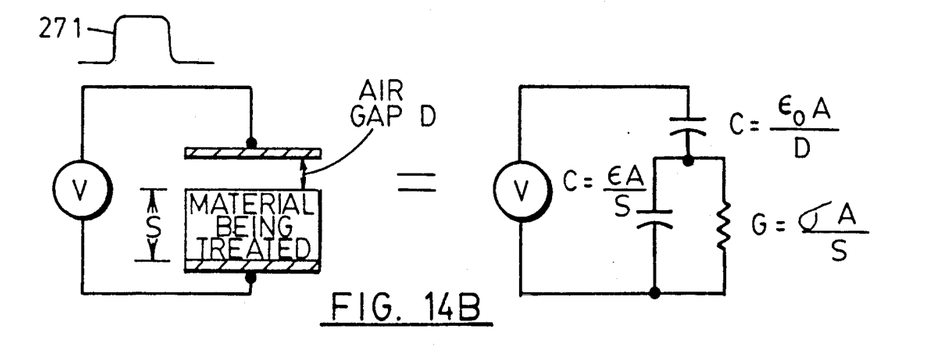

There are a wide variety of combinations of electric field applicators, power source generators and materials. However, two simple configurations are illustrated in FIGS. 14A and 14B. FIG. 14A shows an equivalent circuit for an applicator which is in direct contact with a liquid which contains microorganisms to be treated with a unipolar flat-top pulse 271 of a suitable pulse width and field intensity. FIG. 14B shows an equivalent circuit for a contaminated material which is excited by an electrode separated from the material by an air gap or thin dielectric. FIG. 14B is the same as FIG. 14A except for an additional capacitance 273. The excitation waveform for FIG. 14B is assumed to be a flat-topped pulse 272 of an amplitude of 3000 v/cm in the material to be treated.

In the case of FIG. 14B, the waveform 272 of the applied voltage, V, must be continuously increased with time to compensate for the voltage drop across the capacitance 273 between the electrode and the material under treatment. This air gap represents the principal current limiting effect and therefore the charging of this capacitance or air gap dominates the requirements for the power source. Thus, to determine the amplitude and waveform requirements for the voltage source, we need only to determine the voltage drop across this capacitive element.

Thus, the voltage, V, across a capacitor, C, with an area of A, being charged by a current I(t) is given by:

$$V(t) = \frac{1}{C} \int_0^t I(t)dt \qquad (11)$$

where I(t) is defined by:

$$I(t) = \sigma_i E_i(t) A \qquad (12)$$

where
I(t) is the time-history of the current in the material being treated,
$\sigma$ is the conductivity of the material,
$E_i(t)$ is the required electric field intensity, and
A is the area of the gap.

Based on the examples shown in FIGS. 14A and 14B, we can develop some feel as to the feasibility for each type of application system. In Table i we envision for simplicity a small cubic centimeter of material with conductivities ranging from sea water down to relative dry materials. In addition, if the electrodes are in direct contact with the solution in the form of a

TABLE 1

Example relating to FIG. 14B
Treatment volume is 1 cm × 1 cm × 1 cm cube
Air gap thickness between flat electrode and top of cube is d, where d=0.1 cm and area of gap is A cm²
Dielectric parameters of gap: $\sigma=0$, $\epsilon=10^{-13}$ fd/cm $$C = \frac{\epsilon A}{d} = 10^{-13} \frac{fd}{cm} \frac{1 \text{ cm}^2}{0.1 \text{ cm}} = 10^{-12} fds$$

Dielectric parameters of material $\sigma_i = 10^{-2}$ to $10^{-5}$ mhos/cm
Desired field intensity of voltage across the material portion of the cube: 3000 V/cm or 3000 V
Resulting current through cube:

$$I_i = E_i \sigma_i = 3000 \text{ V/cm} \times 10^{-2} \text{ mhos/cm} = 30 \text{ A/cm}^2$$

$$\begin{aligned}V_d(t) &= \frac{1}{C} \int_0^{t=10^{-6}} E_i \sigma_i dt = \frac{1}{10^{-12}} 30 \text{ A/cm}^2 (10^{-6}) \\ &= 3 \times 10^7 \text{ volts for } \sigma_i = 10^{-2} \text{ mhos/cm} \\ &= 3 \times 10^6 \text{ volts for } \sigma_i = 10^{-3} \text{ mhos/cm} \\ &= 3 \times 10^5 \text{ volts for } \sigma_i = 10^{-4} \text{ mhos/cm} \\ &= 3 \times 10^4 \text{ volts for } \sigma_i = 10^{-5} \text{ mhos/cm}\end{aligned}$$

parallel plate of about 1 cm separation, under these conditions, the field intensity must be in the order of 3,000 v/cm over a duration of about 1 microsecond.

On the other hand, if a 0.1 cm thick air gap is employed, excessive source voltages are required as shown in Table 1 for the more highly conducting media.

In the case of treating solid materials such as oranges, an extension of the study presented in Table I will show that as the conductivity of the fluid surrounding the oranges is increased from a low value to a value comparable to the conductivity of the oranges, the maximum voltage requirement for the source will decrease. Similarly, the energy requirements will also decrease. If the conductivity of the fluids surrounding the oranges is increased beyond that for the conductivity of the oranges, the source voltage requirement will remain about the same but the energy requirements will rise owing to the losses associated with currents which flow around the oranges. Thus, the magnitude of this specific admittance of fluids surrounding solid materials should be similar to the magnitude of the specific admittance of the solid particles being treated. Preferably, the loss tangent of the specific admittance of the surrounding fluids should be as low as possible, thereby allowing recovery of energy which would otherwise be dissipated in the surrounding fluids. In the case of lossy dielectrics, the conductivity of the surrounding fluids should be no less than 1/30th and no more than 10 times that of the material being treated.

If it is not possible to immerse the subject material in a liquid of comparable dielectric values, immersing it in gases which have a relatively high dielectric constant might also be considered. Use of such gases will suppress the electrical breakdown and thereby allow the application of very high field intensities without electrical breakdown or arc-over.

Another method to avoid electrical breakdown is to reduce the duration or length of the pulse to a time short enough to prevent the onset of electron avalanche which leads to an arc-over effect. For example, if an electrical pulse is applied to a pair of closely spaced electrodes, it takes some time for the ionization to build up, especially in liquids. Typically this is in the order of a microsecond for many types of electrode configurations.

In place of a liquid, a foam type material might also be used to cover any solid material to be processed. This foam would have a conductivity and relative dielectric constant which can be tailored to the application at hand. Adding free electrons, via the introduction of sodium chloride or potassium chloride, might also be appropriate. Later on, after the material has been treated, the foam can be removed.

In the case of non-contacting processing where the material surrounding the material to be processed is gas rather than liquid, the use of energy recovery systems are needed to recover the stored energy in the capacitance between the material under treatment and the electrodes. If this is not done, severe power dissipation will occur and make the system impractical.

Figure 15:
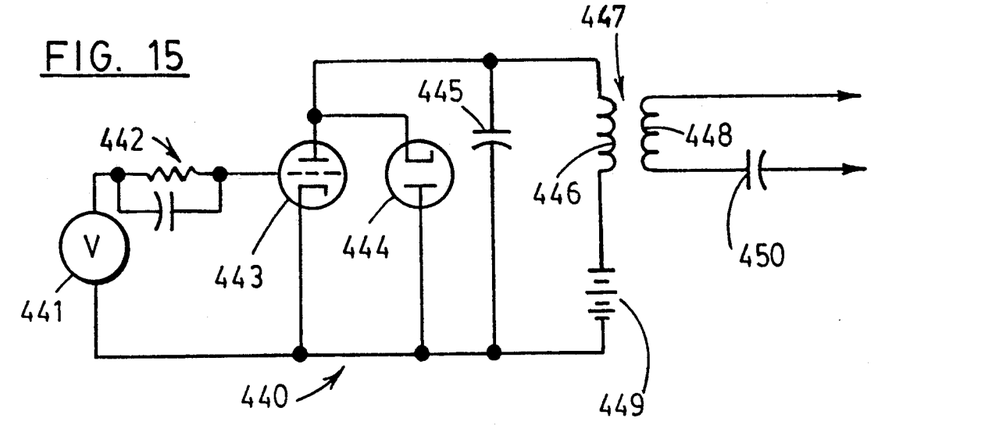
FIG. 15 illustrates an energy recovery system usable in the invention.

FIG. 15 is employed to illustrate an energy recovery system suitable to produce very high field intensities. The system shown in FIG. 15 is a pulse source 440 designed to produce unipolar pulses which are applied to a field exciter.

Figure 16A:
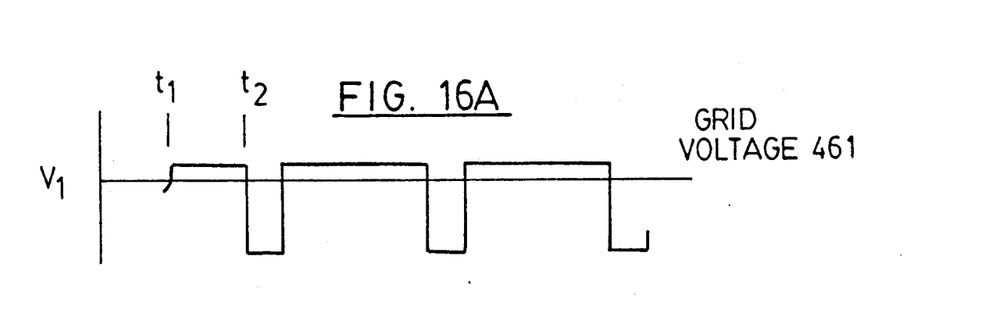
FIGS. 16A through 16C illustrate voltages and currents occurring in the circuit of FIG. 15.
Figure 16B:
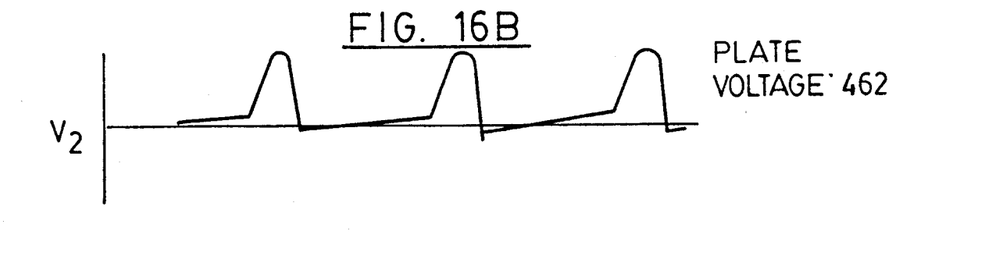
Figure 16C:
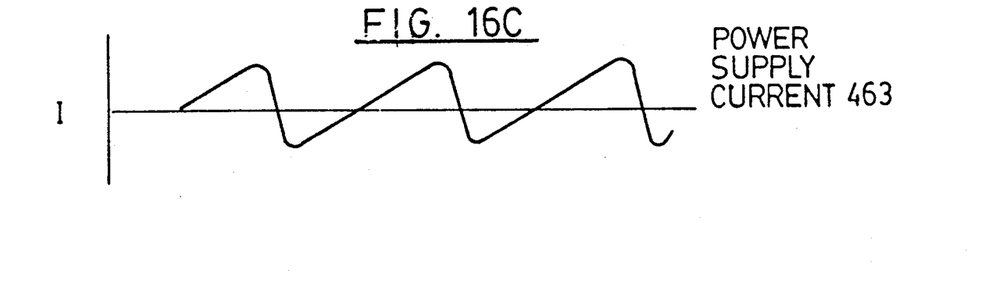

The basic operation of the pulse system 440 is similar to the transistorized deflection system used in some television receivers. It consists of the components as shown in FIG. 15. Assume that a voltage source 441 suddenly turns positive at a time t as shown in the three time histories 461, 462, and 463 of the three different waveforms, respectively grid voltage, plate voltage, and power supply current, of FIGS. 16A, 16B and 16C for the vacuum tube 443 in FIG. 15. In this case the grid current is limited by the grid leak 442 (FIG. 15) but allows sufficient current to flow through the tube 443 such that the current flow is limited by the inductance of the primary 446 of the transformer 447. The inductance is such as to cause a linear rise in current as it flows through the power triode 443. At time $t_2$ (FIGS. 16A–16C) the grid of the triode 443 is driven negative. This causes the voltage across the plate to rise to a very large value. The rate of rise is governed by the resonant frequency as determined by the capacitor 445 (FIG. 15), the stray capacitance of the secondary 448 of the transformer 447, the capacitance 449 of the treatment chamber, and the primary inductance 446 of the transformer. As shown by the waveform 461, FIG. 16A, this resonant frequency is designed to have a duration of the order of 10 microseconds, which produces a pulse width of 5 microseconds. Toward the end of the first half cycle of resonance, the plate of the triode 443 and the cathode of the diode 444 in system 440 are driven negative. This causes the diode 444 to conduct at $t_3$, while at the same time the current 463 (FIG. 16C) is now flowing in the direction which is normally opposite that when initially started at $t_1$. This current flows in the opposite direction into the power supply, thereby recharging it. This phenomenon causes the unexpended energy to be recovered by recharging the battery power supply 449. This recharging continues until the current through the diode 444 goes to zero. Thereafter, the current flow reverses its direction and recharges the inductance 446 through the triode 443 which is then driven in a conducting state. The curve 461 of FIG. 16A shows the waveform of the grid drive voltage source, and the waveform 462 of FIG. 16B shows the voltage across the secondary (or the primary) of the transformer 447. Lastly, the waveform 463 of FIG. 16C shows the current as supplied from the transformer-capacitor combination 447, 450 into the tube-diode circuit. A capacitor 445 of a large value, such that the ac pulse-type waveforms are small, is used to block the corrosion current flow by developing a cathodic protection voltage bias. This bias neutralizes most of the current which leads to electrolytic erosion of the electrodes.

Depending on the susceptibility of viruses to waveforms optimized to destroy bacteria and larger celled life forms, it may be necessary to heat the material to 60° C. briefly to destroy the viruses. Also, the susceptibility of bacteria and other larger-celled organisms to pulsed electric fields is enhanced at higher temperatures. However, the economic key may not always be in elevating the temperature, which could be energy inefficient. Energy can recovered by combining with a counterflow heat exchange process to recover the thermal energy. Such an arrangement is shown in FIG. 1.

In this arrangement, ingressing contaminated liquids at 20° C. are raised to about 52° C. by means of a counterflow heat exchanger which transfers heat from the 60° C. treated liquids. The supplemental heater raises the temperature to 60° C. to kill the viruses. Short unipolar pulses are next applied to destroy the higher life forms. Without the counterflow heat exchanger, the heating costs could be higher and possibly uneconomic.

The above methods and apparatus can, if applied by one skilled in the art, be adapted to other applications where material or fluids must be exposed to high intensity short-duration pulses without arc-over or streamers. Such applications might include exposing liquids containing certain classes of emulsions, to break down the emulsions with little expenditure of energy. Alternatively, the method and apparatus might be used to sensitize microorganisms to certain chemicals or pharmaceuticals, such that less of the chemicals need be used. Further, high intensity short duration pulses are herein defined to have any waveshape. The shape of such a waveform could be a flattopped pulse, an exponentially decaying impulse, or the first half cycle of a sine-wave. Such pulses may be applied sequentially. In some cases the polarity of such pulses may be alternated to mitigate corrosion or ion-exchange effects provided that the duration of the first pulse is sufficiently long.

BIBLIOGRAPHY

Abidor, et al., "Electric breakdown of bilayer lipid membranes I: The main experimental facts and their qualitative discussion." Bioelectrochem. Bioenerget., 6:37-52, 1979; Benz, et al., "Reversible electrical breakdown of lipid bilayer membranes: A charge-pulse relaxation study." J. Membrane Biol., 48:181-204, 1979; Benz, et al., "Pulse-length dependence of the electrical breakdown in lipid bilayer membranes." Blochim. Biophys. Acta, 597:637-642, 1980; Benz, et al., "Relaxation studies on cell membranes and lipid bilayers in the high electric field range. Bioelectrochem. and Bioenerg., 7:723-739, 1980; Chizmadzhev, et al., "Electric breakdown of bilayer lipid membranes III: Analysis of possible mechanisms of defect origination." Bioelectrochem. Bioenerget., 6:63-70, 1979; Cooper, "Gap Junctions increase the sensitivity of tissue cells to exogenous electric fields." J. theor. Biol., 111:123-130, 1984; Crowley, "Electrical breakdown of bimolecular lipid membranes as an electromechanical instability." Biophys. J., 13:711-724, 1973; Dimitrov, "Electric field-induced breakdown of lipid bilayers and cell membranes: A thin viscoelastic film model." J. Membrane Biol., 78:53-60, 1984; Gaylot, "Physical mechanisms of cellular injury in electrical trauma." Ph.D. thesis, MIT, September 1989; Gaylot, et al., "Significance of cell size and tissue structure in electrical trauma." J. theor. Biol., 133:223-237, 1988; Hulsheger, et al., "Electric field effects on bacteria and yeast cells." Radiat. Environ. Biophys. 22:149-162, 1983; Hulsheger, et al., "Killing of bacteria with electric pulses of high field strength." Radiat. Environ. Biophys. 20:53-65, 1981; Hulsheger, et al., "Lethal effects of high-voltage pulses on *E. coli* K12." Radiat. Environ. Biophys., 18:281-288, 1980; Jacob, et al;, "Microbiological implications of electric field effects II. Inactivation of yeast cells and repair of their cell envelope." Zeitschrift fur Allgemeine Mikrobiologic, 21, 3:225-233, 1981; Kinosita, "Formation and resealing of pores of controlled sizes in human erythrocyte membrane." Nature, 268, 4:438-440, 1977; Kinosita, et al., "Hemolysis of human erythrocytes by a transient field." Proc. Natl. Acad. Sci., 74:1923-1927, 1977; Kinosita, et al., "Voltage-induced pore formation and hemolysis of human erythrocytes." Blochim, Biophys. Acta, 471:227-242, 1977; Michael, et al., "The breakdown of electrical insulation in a plane layer of insulating fluid by electrocapillary instability." J. Fluid Mech. pt. 3, 47:609-623, 1971; Neamann, et al., "Gene transfer into mouse lymphoma cells by electropotation in high electric fields." IRI Press Ltd., Oxford, England, 841-845; Powell, et al., "Transient aqueous pores in bilayer membranes: A statistical theory." Bioelectrochem. Bioenerget., 15:211-227, 1986; Sale, "Effects of high electric fields on microorganisms III. Lysis of Erythrocytes and protoplasts." Biochemica et Biophysica Acta, 163:37-43, 1968; Teissie, et al., "Evidence of voltage-induced channel opening in Na/K ATPase of human erythrocyte membrane." J. Membrane Biol., 55:133-140, 1980; Zimmerman, et al., "The development of drug carrier systems: Electrical field induced effects in cell membranes." Biochemistry and Bioenergetics, 7:553-574, 1980; Zimmerman, et al., "Effects of external electric fields on cell membranes." Bioelectrochemistry and Bioenergetics, 3:58-63, 1976; Zimmerman, et al., "Electric field-induced cell-to-cell fusion." J. Membrane Biol., 67:165-182, 1982; Zimmerman, "Electrical breakdown Electropermeabilization and electrofusion," Rev. Physiol. Blochem. Pharmacol., 105:176-256, 1986; Zimmerman, et al., "Cells with manipulated functions New perspectives for cell biology, medicine, and technology." Angew. Chem. Int. Ed. Engl., 20:325-344, 1981; Zimmerman, et al., "Development of drug carrier systems. Electrical field induced effects in cell membranes." Bioelectrochem. Bioenerget., 7:553-574, 1980.

I claim:

1. An energy-efficient electromagnetic method for elimination of noxious biological organisms comprising the steps of:
   (a) conveying a material contaminated with noxious biological organisms into and through an exposure chamber;
   (b) in the exposure chamber, exposing the contaminated material to a spatial non-uniform, high intensity electric field; and
   (c) in the exposure chamber, suppressing excessive current flow in localized regions, including suppressing arcing and current streamers;
   the amplitude of the current density and electric field within the exposure chamber being controlled, in accordance with the conductivity and/or dielectric constant of the contaminated material, so that the electric field intensity is of the order of 3,000 volts/centimeter or more.

2. An energy-efficient method for elimination of noxious biological organisms, according to claim 1, in which, in step (b), the electric field is a pulsed field with the pulses having a duration of 0.2 to 200 microseconds.

3. An energy-efficient method for elimination of noxious biological organisms, according to claim 2, in which the spatial non-uniform electric field of step (b) extends between spaced electrodes, between which the contaminated material traverses the exposure chamber and is exposed to at least a portion of the electric fields.

4. An energy-efficient method for elimination of noxious biological organisms, according to claim 3, in which at least one of the electrodes is coated, on a surface facing the contaminated material, with a layer having an admittance that is no greater than the admittance of the contaminated material.

5. An energy-efficient method for elimination of noxious biological organisms, according to claim 3, in which:
   the two spaced electrodes include an outer, tubular electrode concentric with and encompassing an inner electrode;
   the contaminated material passes through an annular space between the electrodes; and
   the electric field adjacent the inner electrode is at least ten percent stronger that the electric field adjacent the outer electrode.

6. An energy-efficient method for elimination of noxious biological organisms, according to claim 5, in which at least one of the electrodes is coated, on a surface facing the contaminated material, with a layer having an admittance that is no greater than the admittance of the contaminated material.

7. An energy-efficient method for elimination of noxious biological organisms, according to claim 3, and including the following additional step:
   (d) pretreating the contaminated material to remove major heterogeneities.

8. An energy-efficient method of elimination of noxious biological organisms, according to claim 3, and including the following additional step:
   (e) increasing the temperature of the contaminated material to about 40° C. to 60° C.

9. An energy-efficient method for elimination of noxious biological organisms, according to claim 3, and including the following additional steps:
   (f) sensing and determining the specific admittance and the current density of the materials within the exposure chamber; and
   (g) controlling the electrical current used to generate the electric field of step (b) to assure maintenance of the requisite field intensity.

10. An energy-efficient method for elimination of noxious biological organisms, according to claim 3, and including the following additional steps:
    (d) pretreating the contaminated material to remove major heterogeneities;
    (e) increasing the temperature of the contaminated material to about 40° C. to 60° C.;
    (f) sensing and determining the specific admittance and the current density of the materials within the exposure chamber; and
    (g) controlling the electrical current used to generate the electric field of step (b) to assure maintenance of the requisite field intensity.

11. An energy-efficient method for elimination of noxious biological organisms, according to claim 3, and including the following additional steps, prior to step (a):
    (h) comminuting a product contaminated with noxious biological organisms; and
    (i) mixing the comminuted product from step (h) with a fluid of predetermined electrical properties to form the contaminated material for step (a).

12. An energy-efficient method for elimination of noxious biological organisms, according to claim 11, and including the following additional step:
    (j) separating the comminuted product from the fluid of step (i), following treatment in the exposure chamber.

13. An energy-efficient method for elimination of noxious biological organisms, according to claim 3, and including the following additional step:
    (k) coating the contaminated material with a flexible material having a similar specific admittance prior to step (a).

14. An energy-efficient method for elimination of noxious biological organisms, according to claim 12, and including the following additional step:
    (k) coating the contaminated material with a flexible material having a similar specific admittance prior to step (a).

15. An energy-efficient method for elimination of noxious biological organisms, according to claim 1, for a contaminated material having a loss tangent of 0.6 or less, including the following additional step:
    (l) recovering excess energy from the lossless portion of the exposure chamber.

16. An energy-efficient method for elimination of noxious biological organisms, according to claim 3, and including the following additional steps:
    (d) pretreating the contaminated material to remove major heterogeneities;
    (f) sensing and determining the specific admittance and the current density of the materials as appearing within the exposure chamber; and
    (g) controlling the electrical current used to generate the electric field of step (b) to assure maintenance of the requisite field intensity.

17. An energy-efficient method for elimination of noxious biological organisms, according to claim 3, and including the following additional step:
    (k') coating the contaminated material with a flexible material having a similar specific admittance of no less than 1/30th and no more than 10 times the specific admittance of the contaminated material.

18. An energy-efficient method for elimination of noxious biological organisms, according to claim 3, in which a low-voltage continuous direct current voltage is applied to the exposure chamber to inhibit corrosion by transfer of ions from the permanent components within the exposure chamber to the fluids passing through the exposure chamber.

19. An energy-efficient method for elimination of noxious biological organisms, according to claim 10, and including the additional step of transferring some heat from the treated fluids to the untreated fluids by means of a counterflow heat exchanger.

* * * * *